US00PP29345P3

(12) United States Plant Patent
Monge

(10) Patent No.: US PP29,345 P3
(45) Date of Patent: May 29, 2018

(54) ***SANSEVIERIA* PLANT NAMED 'FROZEN'**

(50) Latin Name: *Sansevieria trifasciata*
Varietal Denomination: FROZEN

(71) Applicant: Luis Carlos Monge, Pavones (CR)

(72) Inventor: Luis Carlos Monge, Pavones (CR)

(73) Assignee: Fleurizon, LLC, Camarillo, CA (US)

( * ) Notice: Subject to any disclaimer, the term of this patent is extended or adjusted under 35 U.S.C. 154(b) by 0 days. days.

(21) Appl. No.: 15/330,682

(22) Filed: Oct. 25, 2016

(65) Prior Publication Data

US 2018/0116090 P1 Apr. 26, 2018

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./382
See application file for complete search history.

*Primary Examiner* — Susan McCormick Ewoldt
(74) *Attorney, Agent, or Firm* — Cassandra Bright

(57) ABSTRACT

A new and distinct *Sansevieria* cultivar named 'FROZEN' is disclosed, characterized by a unique plant structure of more evenly resetting foliage forming a center "nest" shape. Foliage is strong and fibrous, dark green and heavily covered with blotches and striations of blended lighter green. Shape of the foliage is uniquely deltate, plants are semi-compact. The new variety is a *Sansevieria*, typically produced as an indoor ornamental plant.

2 Drawing Sheets

Figure 1:
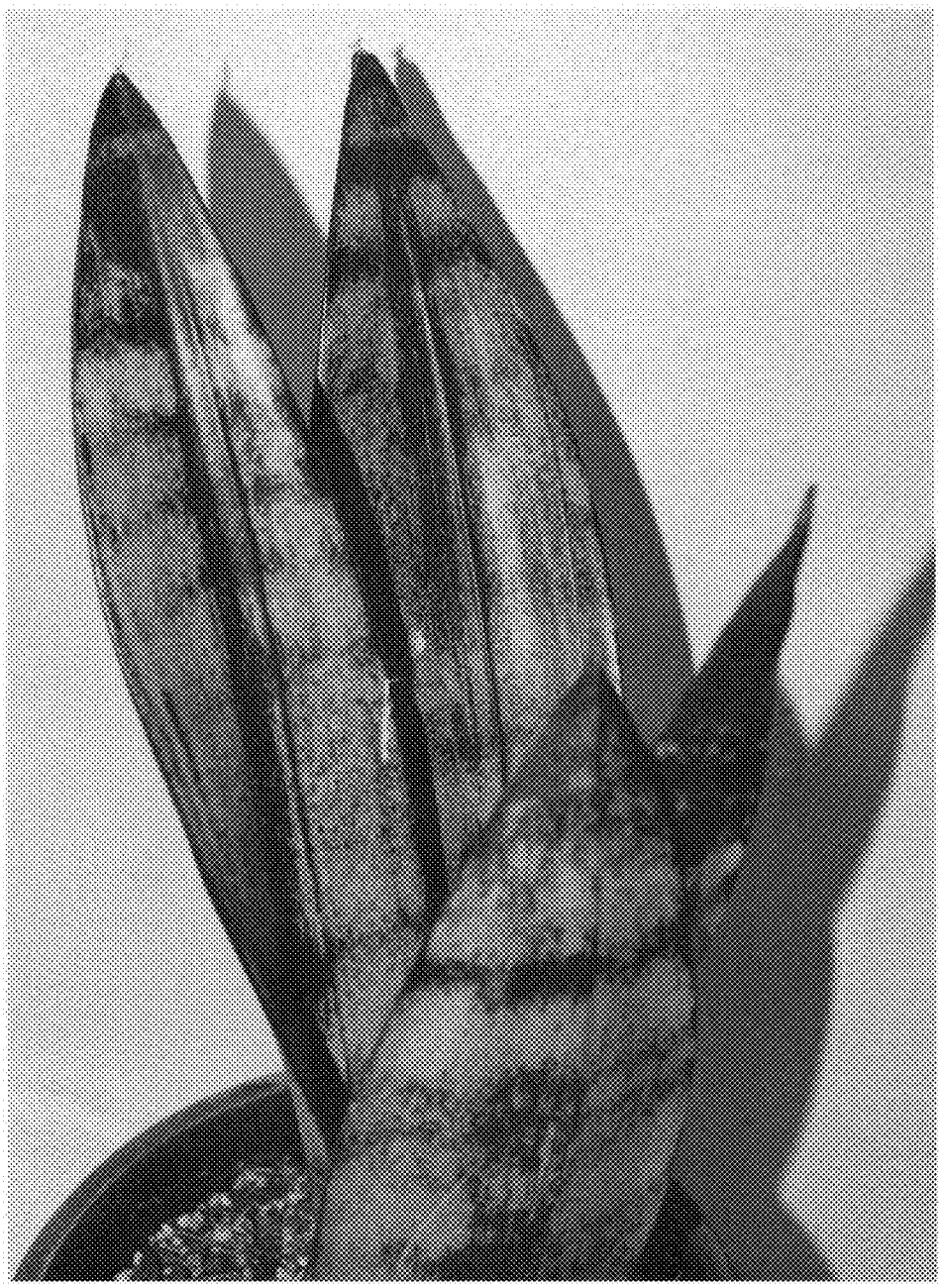

Latin name of the genus and species: *Sansevieria trifasciata.*

Variety denomination: 'FROZEN'.

BACKGROUND OF THE INVENTION

This application relates to a new cultivar of *Sansevieria trifasciata*. The new variety is the product of chance discovery. The inventor discovered the new variety as a whole plant, naturally occurring mutation from the parent plant *Sansevieria trifasciata* 'Zeylanica', unpatented.

The new variety was first observed by the inventor, in 2013 in a planting of the parent plants, at a commercial nursery in Costa Rica. After identifying the new variety as a potentially interesting selection, the inventor continued confidential testing and propagation of 'FROZEN', assessing stability of the unique characteristics of this variety.

Asexual reproduction of the new cultivar 'FROZEN' was first performed at a commercial nursery in Sector Turrialva, Costa Rica by leaf cuttings of original plant in 2013. Through subsequent propagation, approximately 4 generations have been reproduced, which have shown that the unique features of this cultivar are stable and reproduced true to type.

SUMMARY OF THE INVENTION

The cultivar 'FROZEN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FROZEN'. These characteristics in combination distinguish 'FROZEN' as a new and distinct *Sansevieria* cultivar:

1. Unique plant structure, more evenly rosetting than typical of *Sansevieria*, forming a kind of center "nest".
2. Foliage is very dark green, heavily covered with light green horizontal striations.
3. Plants produce more leaves per plant on average.
4. Deltate leaf shape.
5. Semi-compact *Sansevieria* variety.
6. Foliage is strong and fibrous.

PARENT COMPARISON

Plants of the new cultivar 'FROZEN' are similar to the parent variety, in many horticultural characteristics. However the new variety, 'FROZEN' differs from parent in the following characteristics:

1. The parent variety does not have tough, fibrous foliage as found in the new variety.
2. Plants of the new variety are shorter than plants of the parent.
3. The new variety has more blended, less defined striations.
4. Plants of the new variety produce more leaves per plant than the parent variety.
5. Plants of the new variety produce a uniquely defined rosette not seen in the parent variety.

COMMERCIAL COMPARISON

The new variety can be compared to the unpatented commercial variety *Sansevieria* 'Futura Robusta'. Plants of 'Frozen' differ from 'Futura Robusta' in the following characteristics:

1. Plants of the new variety are shorter and more compact.
2. Foliage of the new variety has a narrower diameter.
3. Foliage of the new variety is glossy, foliage of 'Futura Robusta' is matte in appearance.

4. Foliar striation pattern of the new variety is more blended and less definite than that of 'Futura Robusta'.
5.

'FROZEN' can be compared with the unpatented commercial variety *Sanservieria*. 'Black Coral', unpatented. However the new variety, 'FROZEN' differs from 'Black Coral' in the following characteristics:

1. Foliage of the new variety is stronger, more fibrous and resistant to breakage then foliage of the comparator.
2. Foliage of the new variety is more fully covered light colored striations.
3. Foliage of the new variety is wider than that of the comparator.
4. Plants of the new variety produce a unique, even rosette not seen in plants of 'Black Coral'.
5. Plants of the new variety are shorter than plants of 'Black Coral'.

BRIEF DESCRIPTION OF THE PHOTOGRAPHS

The accompanying photograph in FIG. 1 illustrates in full color a typical plant of 'FROZEN' grown in a commercial greenhouse in Costa Rica. The plant is in a 1 gallon pot, at approximately 4 months old.

Figure 2:
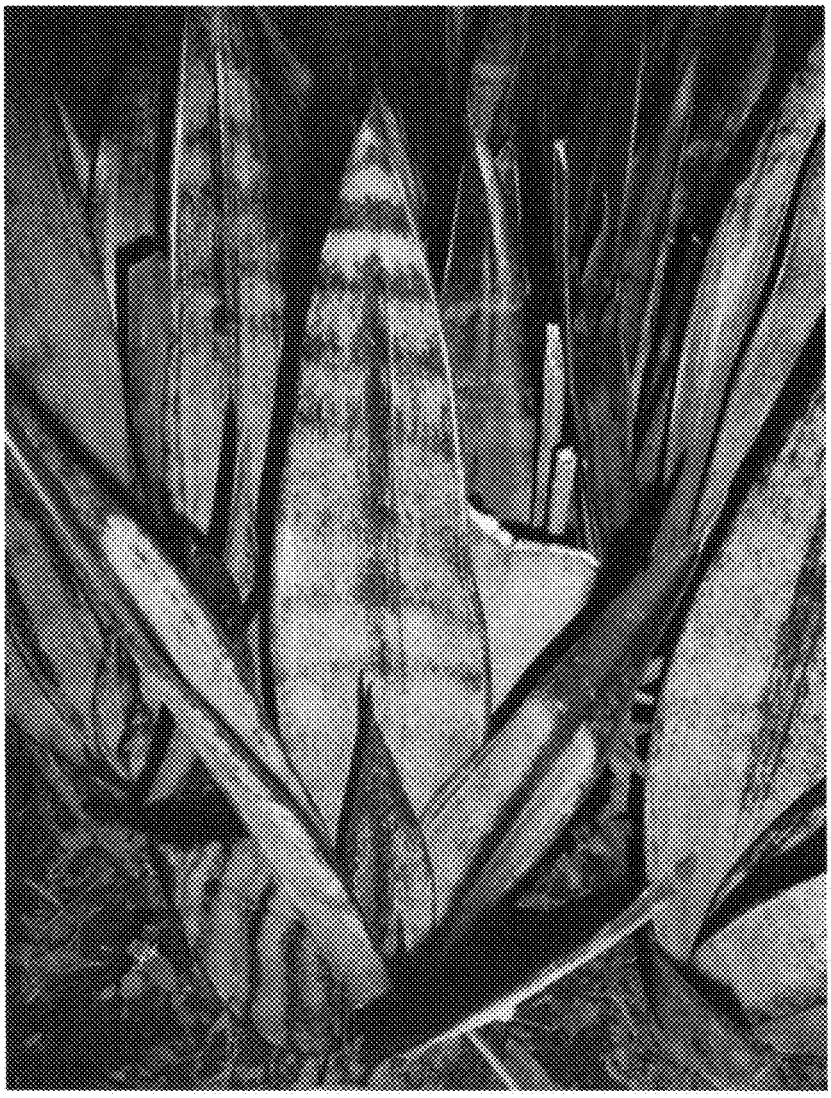

FIG. 2 illustrates a more mature plant, forming the nest like rosette. The plant in FIG. 2 was grown in the ground.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'FROZEN' plant is grown in Florida. The plant is approximately 5 months old in a 6 inch pot. Temperatures ranged between 22° C. to 40° C. during the day and 15° C. to 30° C. at night. No chemical treatments were given to the plants. Measurements and numerical values represent averages of typical plant types.

Botanical classification: *Sansevieria trifasciata* 'FROZEN'.

PROPAGATION

Time to initiate rooting: About 2 to 3 months at approximately 17° C. to 40° C.

Root description: Moderately thick, slightly fleshy, slightly fibrous, moderately dense, moderately branched, colored greyed-orange, near RHS N170B.

PLANT

Growth habit: Monopodial, evenly rosulate, compact, short *Sansevieria*.

Height: Approximately 27.5 cm.

Plant spread: Approximately 21.0 cm.

Growth rate: Moderate. Approximately 5 cm per month.

Number of leaves per plant of the above age: Average: 6.

FOLIAGE

Leaf:

*Arrangement*.—Evenly rosulate, "nest" formation.

*Average length*.—Average range 15 to 25 cm.

*Average width*.—Average range 5 to 7 cm.

*Depth (thickness) of leaf blade*.—Approximately 2 to 3 mm, somewhat succulent.

*Shape of blade*.—Narrow deltate.

*Blade aspect*.—Leaves in interior of rosette moderately curved inward, more pronounced towards base, or with a slight twisting. Outermost leaves nearly flat, very slightly concave.

*Growth aspect*.—Leaves grow at a slight outward angle.

*Apex*.—Apiculate, nearly sharp to the touch.

*Base*.—Decurrent.

*Margin*.—Entire.

*Texture of top surface*.—Glabrous, 1 to 3 pronounced ribs towards center of blade.

*Texture of bottom surface*.—Glabrous.

*Appearance of top surface*.—Shiny.

*Appearance of bottom surface*.—Matte.

*Color*.—Young foliage upper side: Main color between Green 139A and Yellow-Green 147A. Large center stripe between 139A and 147A. Large linear blotches/blended striations near Yellow-Green 147D cover approximately 30% of blade. Young foliage under side: Main color between Green 139A and Yellow-Green 147A. Large center stripe between 139A and 147A. Large linear blotches near Yellow-Green 147D cover approximately 30% of blade. Mature foliage upper side: Background color between Green 139A and Yellow-Green 147A Large linear blotches/blended striations near Yellow-Green 147D cover approximately 70% of blade. Mature foliage under side: Background color between Green 139A and Yellow-Green 147A Large linear blotches near Yellow-Green 147D cover approximately 70% of blade.

*Venation*.—Type: Parallel. Color: Upper side: Indistinguishable from leaf blade. Under side: Indistinguishable from leaf blade.

Sheath:

*Average length*.—Approximately 2.0 cm.

*Average width*.—Approximately 4 cm (clasping leaf base).

*Color*.—Green 139A.

*Texture*.—Glabrous, moderately glossy.

Other distinguishing characteristics: Leaf is very strong and fibrous, resists breakage.

OTHER CHARACTERISTICS

Disease resistance: Neither resistance nor susceptibility to the normal diseases found in *Sansevieria* has been observed.

Fruit/seed production: No fruits/seeds detected to date.

What is claimed is:

1. A new and distinct cultivar of *Sansevieria* plant named 'FROZEN' as herein illustrated and described.

* * * * *